United States Patent [19]

Deming et al.

[11] Patent Number: 4,458,541
[45] Date of Patent: Jul. 10, 1984

[54] LIQUID SAMPLE INJECTION VALVE FOR GAS CHROMATOGRAPHS

[75] Inventors: Philip L. Deming, Whittier; Carl A. Farren, Placentia, both of Calif.

[73] Assignee: Beckman Instruments, Inc., Fullerton, Calif.

[21] Appl. No.: 495,918

[22] Filed: May 23, 1983

Related U.S. Application Data

[62] Division of Ser. No. 311,092, Oct. 13, 1981, abandoned.

[51] Int. Cl.³ ............................................. G01N 1/10
[52] U.S. Cl. ............................. 73/863.11; 73/863.73; 73/864.83
[58] Field of Search ........... 73/863.11, 863.54, 863.72, 73/863.73, 863.83, 864.81, 864.83, 61.1 C; 210/656

[56] References Cited

U.S. PATENT DOCUMENTS

| | | | |
|---|---|---|---|
| 3,401,565 | 9/1968 | Stoll et al. | 73/863.83 |
| 3,463,012 | 8/1969 | McKinney et al. | 73/863.11 |
| 3,581,573 | 6/1971 | Purcell et al. | 73/863.11 |
| 3,643,511 | 2/1972 | Warncke et al. | 73/863.83 |
| 4,289,029 | 9/1981 | Sampson et al. | 73/863.11 |
| 4,356,733 | 11/1982 | Braunweiler | 73/863.83 |

*Primary Examiner*—S. Clement Swisher
*Assistant Examiner*—John E. Chapman, Jr.
*Attorney, Agent, or Firm*—R. J. Steinmeyer; P. R. Harder; E. C. Jason

[57] ABSTRACT

An improved liquid sample injection valve having a metering rod for receiving a sample of a test liquid in a sample loading assembly and delivering that sample to a sample evaporating assembly that is connected to a gas chromatograph. In the sample loading assembly there is provided a sample chamber housing having an improved sealing and mounting arrangement that provides a high degree of thermal isolation between the sample loading and evaporating assemblies. A novel mounting arrangement for the metering rod allows the latter to be conveniently changed without disassembling the valve. The sample evaporating assembly is provided with a flow control element which minimizes deal volume and provides improved sample removal and evaporation characteristics.

16 Claims, 2 Drawing Figures

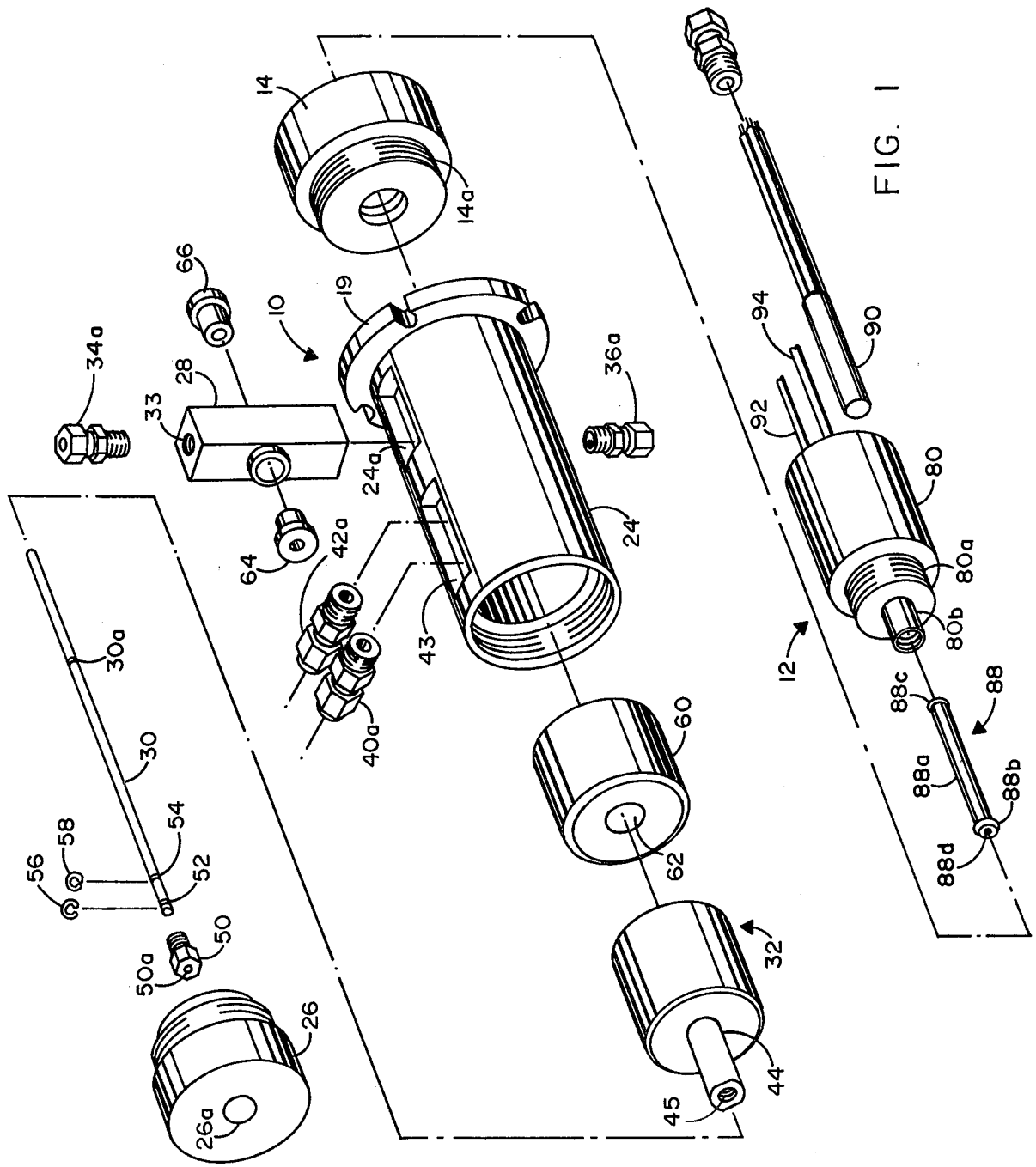

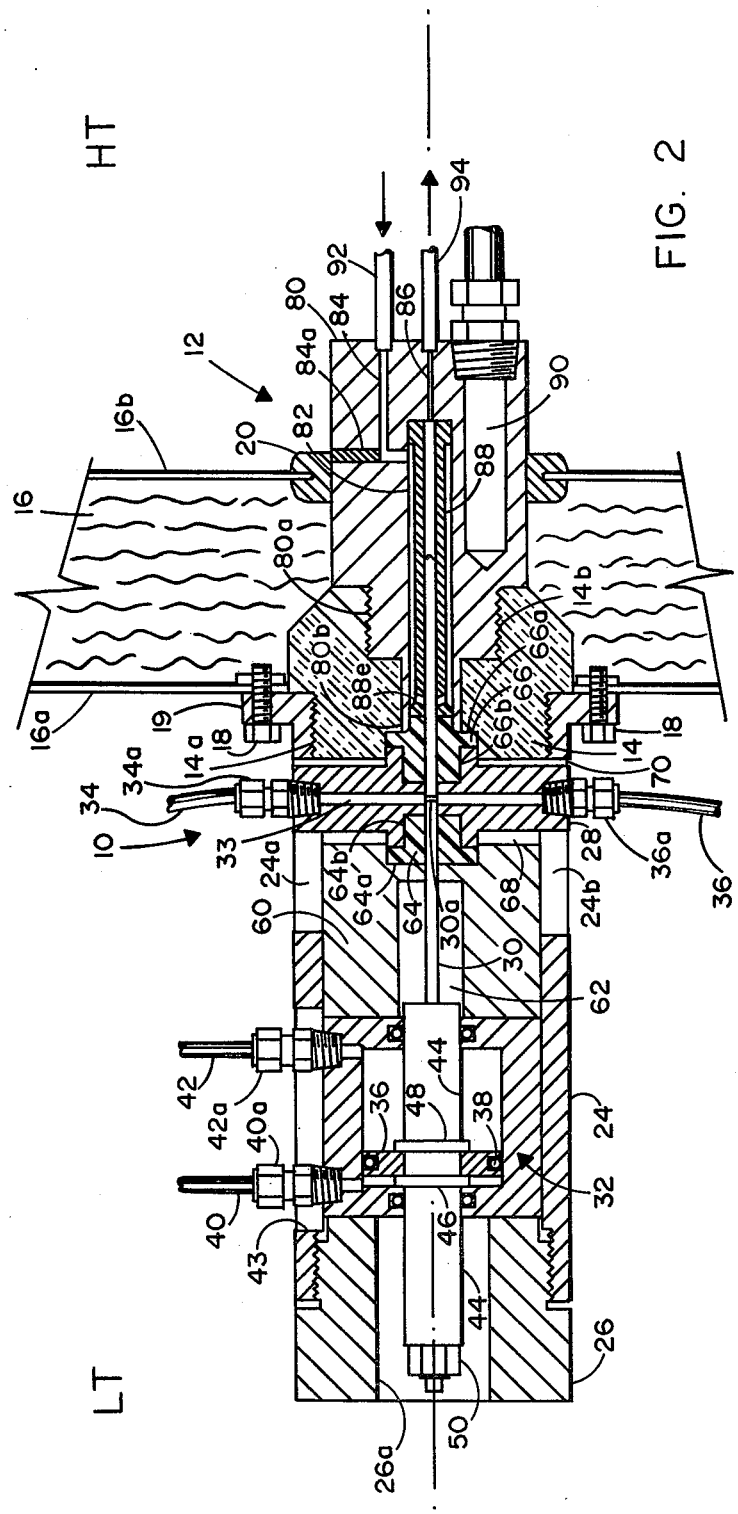

LIQUID SAMPLE INJECTION VALVE FOR GAS CHROMATOGRAPHS

This is a division of application Ser. No. 06/311,092, filed Oct. 13, 1981, and now abandoned.

BACKGROUND OF THE INVENTION

Under circumstances where it is necessary to separate and measure the concentrations of components of a mixture, one commonly used instrument is a gas chromatograph. In such instruments, a sample in the vapor phase is injected into a carrier gas stream which transports the sample to a chromatographic column. Within this column the carrier gas continues to pass at a uniform rate while the components of the sample are retained at rates that depend upon a number of factors. Understanding these factors is a study beyond the scope of this invention. The differences in these retention values cause the various components of the sample to separate into bands which travel through the column at characteristic rates. This, in turn, allows the distribution of the components to be determined from the location and size of the bands.

In order to increase the rate at which samples of test liquids may be processed through a gas chromatograph, it is customary to use a device known as a liquid sample injection valve. The latter valve automates the process of taking a sample of the test liquid and delivering the same for vaporization in the presence of the carrier gas stream of the gas chromatograph. Valves of this type typically include a pneumatically driven metering rod that reciprocates between a low temperature sample loading assembly and a high temperature sample evaporating assembly.

Since the metering rod carries a sample in a sample cavity or groove having a known volume, it is important that the temperature of the metering rod be held constant. This is because temperature differences can cause the density of the sample to vary resulting in erroneous concentration readings. Additionally, it is desirable to keep the sample flowing past the sample cavity or groove at a low temperature to reduce the danger of handling flammable liquids, to comply with the law (e.g. Germany), and to avoid formulation of bubbles at the sample cavity or groove which would affect sample size. It follows, then, that neither the proximity of the low temperature sample loading assembly, nor the reciprocation of the metering rod therebetween, can be allowed to affect the maintenance of a constant temperature at the sample cavity or groove which is substantially lower than that of the sample evaporation assembly.

In attempting to meet the foregoing requirements, various types of liquid sample injection valves have been developed. One of these valves is described in U.S. Pat. No. 3,401,565 issued on Sept. 17, 1968 in the name of E. H. Stoll et al. The latter patent describes a valve in which the desired thermal isolation between the sample loading and evaporating assemblies is provided by connecting these assemblies through a relatively long and narrow neck that is wrapped with cooling coils which carry a flow of a liquid coolant. While this structure provided the desired thermal isolation, it also resulted in the need for relatively long fluid seals for the metering rod, and in the concentration of excessive mounting stresses in vicinity of the connecting neck. Other problems with such valves included the presence of dead volumes, i.e., spaces within which portions of a sample could accumulate and contaminate subsequently injected samples, and the difficulty of adjusting the pressure on or replacing the seals associated with the metering rod.

Another type of liquid sample injection valve is described in U.S. Pat. No. 3,643,511 issued on Feb. 22, 1972 in the name of Warncke et al. In valves of the latter type the desired thermal isolation between the sample loading and evaporating assemblies was afforded by constructing the sample chamber housing from a flexible insulating material. In addition, the pressure on the seals associated with the metering rod was made adjustable by compressing the entire sample chamber housing. One problem with this structure was that the compression of the sample chamber housing induced therein stresses that could in time result in leaks between the sample chamber housing and the inlet and outlet fittings associated therewith. Another problem was that, like the valve described in the Stoll patent, the valve of the Warncke patent included a narrow neck which provided only a weak structural connection between the sample loading and evaporating assemblies.

SUMMARY OF THE INVENTION

In accordance with the present invention, there is provided a liquid sample injection valve which incorporates a number of improvements to both the sample loading assembly and the sample evaporating assembly. One respect in which the sample loading assembly is improved over the corresponding assemblies of prior valves is the inclusion therein of a sample chamber housing which absorbs heat relatively slowly from the sample evaporating assembly and which dissipates heat readily to the environment of the sample loading assembly. This improved structure helps to maintain the temperature of the sample liquid at or near the ambient temperature, in spite of the close proximity of the sample evaporating assembly.

A second improvement to the sample loading assembly is the provision therein of an improved metering rod mounting arrangement. By means of this arrangement the mounting fastener of the metering rod is made easily accessible to the user. This improved accessibility, in turn, facilitates the disconnection and replacement of the rod. As a result, a metering rod having a sample cavity of one size may be easily and quickly replaced with a metering rod having a sample cavity of a different size.

One respect in which the sample evaporating assembly is improved over the corresponding assemblies of prior valves is the inclusion therein of a carrier gas flow control element. By means of this element, there is eliminated both substantially all of the dead volume within the evaporating assembly, and the need for providing long carrier gas flow passages through the evaporating assembly housing. The latter feature, in turn, allows the evaporating assembly housing to have a cross-sectional area which decreases in the direction of the sample loading assembly, resulting in a reduction in the rate at which heat flows from the evaporating assembly to the loading assembly.

An additional advantage of the flow control element is that, by virtue of its removability, the openings through which carrier gas is directed against the sample are made conveniently accessible for cleaning purposes. The flow control element also allows these openings to be arranged so that carrier gas is directed against the sample in one or more discrete jets, the number and angles of which may be changed by simply changing the flow control elements. This, in turn, assures that the vaporization characteristics of the valve may be tailored to different types of samples to assure optimal performance in a variety of applications.

Still another structural improvement to the liquid sample injection valve of the invention is the inclusion therein of a rigid valve junction block that is composed of an insulating material and that is secured to both the sample loading assembly and the sample evaporating assembly. Because of the use of the above-described types of loading and evaporating assemblies, this valve junction block may be made massive enough to provide a mechanically strong, thermally nonconductive structural bridge between the assemblies, without resulting in an increase in the dead volume within the evaporating assembly.

Other advantages and features of the present invention will be apparent from the following description and drawings.

DESCRIPTION OF THE DRAWINGS

FIG. 1 is an exploded perspective view of the preferred embodiment of the present invention, and FIG. 2 is a cross-sectional assembled view of the embodiment of FIG. 1.

DESCRIPTION OF THE PREFERRED EMBODIMENTS

Referring to FIG. 1, there is shown a liquid sample injection valve having a sample loading assembly 10 and a sample evaporating assembly 12. These assemblies are preferably attached to and mounted on opposite ends of a valve junction block 14 by means of threads 14a and 14b (see FIG. 2), respectively. As is best seen in FIG. 2, the injection valve as a whole is mounted on an insulating wall 16 which separates the high temperature interior HT of a gas chromatograph (not shown) from the low temperature region LT that surrounds the gas chromatograph. To accomplish this mounting, sample loading assembly 10 may be attached to the exterior covering 16a of wall 16 by suitable bolts 18 and a mounting flange 19, while sample evaporating assembly 12 is sealed against inner covering 16b of wall 16 by a suitable high temperature grommet 20.

Sample loading assembly 10 includes a generally cylindrical metal housing 24 one end of which is threaded to receive an end cap 26 and the other end of which terminates in mounting flange 19. Loading assembly 10 also includes a sample chamber housing 28 which is adapted to be positioned within housing 24 by insertion through a pair of longitudinal slots 24a and 24b therethrough. Finally, loading assembly 10 includes a metering rod 30 that is mounted on and driven by a linear actuator 32, which may comprise a pneumatically driven piston assembly.

When metering rod 30 is in its rest position, i.e., the position shown in FIG. 2, an annular metering groove or sample cavity 30a therein is exposed to the liquid to be sampled by virtue of its position within a passage 33 through housing 28. While rod 30 is in this position, the liquid in metering groove 30a will change continuously as the sample liquid enters passage 33 through a suitable inlet line 34 and coupling 34a and exits passage 33 through an outlet line 36 and coupling 36a. Upon energization of actuator 32, however, metering groove 30a and its contents are transported into sample evaporating assembly 12 for vaporization in the presence of the carrier gas of an associated gas chromatograph. Once groove 30a has been stripped of its sample, metering rod 30 will be returned to its rest position by a reversal in the pneumatic state of actuator 32. It will be understood that this sequence of movements comprises the taking of a single sample and must be repeated as often as necessary to provide the desired chromatographic sampling rate.

The above-described movements of metering rod 30 occur as pneumatic driving pressure is applied to first one and then the other side of a piston 36 which is sealed to the interior of the housing of actuator 32 by an O-ring 38. During the forward or inward movement of piston 36 and metering rod 30, driving pressure is applied through a pneumatic line 40 and removed through pneumatic line 42. During the reverse or outward movement of piston 36 and metering rod 30, driving pressure is applied through pneumatic line 42 and removed through pneumatic line 40. Since actuator 32 and the fluidic devices (not shown) that establish and control the flow of gas therethrough are conventional, these devices will not be described herein.

In the preferred embodiment actuator 32 is slidably mounted within housing 24. As will be explained more fully later, this mounting allows actuator 32 to serve as a force transmitting medium whereby the longitudinal force produced by the tightening of end cap 26 may be transmitted to the seals that are associated with housing 28.

In accordance with one feature of the present invention, piston 36 is penetrated by a hollow rod 44 which is fastened thereto by means of retaining rings 46 and 48. This arrangement allows metering rod 30 to extend through piston assembly 36-44 and to be connected thereto at the user accessible (outer) end thereof. More particularly, as is best seen in FIG. 1, metering rod 30 is held in place in the central hole 50a of a bolt 50, by grooves 52 and 54 and retaining rings 56 and 58. The latter structure is then fastened to the outer end of the piston assembly via the threaded hole 45 in rod 44. The advantage of this fastening arrangement is that it permits a user to replace metering rod 30 with a metering rod having a metering groove of a different size, without having to disassemble the sample loading assembly 10.

If, for example, rod 44 and bolt 50 extend far enough into the hole 26a in end cap 26, metering rod 30 may be removed by simply loosening bolt 50 and sliding it and metering rod 30 out of loading assembly 10. Ordinarily, however, it is preferable that rod 44 and bolt 50 be recessed a small distance from the outer end of hole 26a for safety reasons. Even where this is the case, however, it is then merely necessary to unscrew end cap 26 and then remove metering rod 30 in the just-described manner. Thus, it will be seen that the present invention allows a metering rod to be removed and replaced with a metering rod having a different groove size with a minimum of effort and without any substantial disassembly of the sample loading assembly.

Positioned adjacent to actuator 32 is a spacer element 60 having a central hole 62 which has a diameter greater than that of rod 44, and has a length greater than the longitudinal travel of rod 44 to provide internal clearance so that rod 44 may reciprocate between its innermost and outmost positions without impacting other parts of the sample loading assembly. In the preferred embodiment spacer 60 is slidably mounted within housing 24. As a result spacer 60 can also serve as a force transmitting medium whereby the longitudinal force produced by the tightening of end cap 26 may be transmitted from cap 26 to the seals that are associated with sample chamber housing 28. Since spacer 60 is made necessary only by the inward projection of rod 44, it will be understood that spacer 60 may be eliminated if actuator 32 is of a type not having an inwardly projecting rod. Alternatively, spacer 60 may be regarded as an integral part of actuator 32.

In order to assure that an accurately measured quantity of sample is transported by metering rod 30, stripper seals 64 and 66 are provided for use therewith. The use of the word "stripper" in the name of these seals reflects the fact that they have a squeegee action which assures that substantially only the sample liquid trapped in the sample groove can pass therethrough. Seals 64 and 66 also serve to prevent the sample liquid within sample passage 33 from escaping into the environment. The stripping and sealing action of seals 64 and 66 will now be described.

Referring to FIG. 2, there is shown a first or outer stripper seal 64 which is positioned between spacer 60 and sample chamber housing 28, and a second or inner stripper seal 66 which is positioned between sample chamber housing 28 and junction block 14. First stripper seal 64 is preferably mounted in the space formed by shallow circular recesses 64a and 64b in spacer element 60 and sample chamber housing 28, respectively. Similarly, second stripper seal 66 is preferably mounted in the space formed by circular recesses 66a and 66b in junction block 14 and sample chamber housing 28, respectively. These recesses assure an accurate positioning of the seals with respect to rod 30 and housing 28.

In the preferred embodiment, housing 28 is fixed in position within sample loading assembly 10 as a result of its being trapped between seals 64 and 66. In other words, sample chamber housing 28 is mounted by the seals at the ends thereof and has only an incidental slidable contact with either spacer 60 or junction block 14. It will be understood that it is desirable that the area of the metal to metal contact between housing 28 and spacer 60 be as small as is practicable in order to minimize the rate at which heat can flow into housing 28 by metallic conduction through housing 24 and spacer 60. In critical applications, the raised rim on one or both of recesses 64b and 66b of housing 28 may even be eliminated entirely.

The above-described mounting arrangement allows housing 28 to be held firmly in place within assembly 10 even though a first air gap 68 exists between spacer element 60 and one end of housing 28, and a second air gap 70 exists between valve junction block 14 and the other end of housing 28. These air gaps are desirable because they allow ambient air currents to flow over the exterior of sample chamber housing 28 to help maintain housing 28 at the ambient temperature in spite of its proximity to insulating wall 16. Air gaps 68 and 70 are also desirable because they serve as barriers to the flow of thermal energy from insulating wall 16 and evaporating assembly 12 to loading assembly 10.

The above-described air gaps and minimal metal to metal contact between housing 28 and spacer 60, coupled with the use of low conductivity materials for junction block 14 and seals 64 and 66, together assure that housing 28 does not appreciably heat the sample liquid in sample passage 33. As previously explained, this is highly desirable since it assures that the valve of the present invention does not introduce sampling errors by changing the volume or density of the sample in metering groove 30a. These same characteristics also assure that the desired high evaporating temperature within assembly 12 is not adversely affected by heat leaking therefrom into sample loading assembly 10. Thus, the present invention assures that neither sample chamber housing 28 nor evaporating assembly 12 is adversely affected by the flow of heat therebetween in spite of their close proximity.

As sample loading assembly 10 is being put together, housing 28 is inserted into housing 24 by sliding the same, with stripper seals 64 and 66 in place, through slots 24a and 24b. Spacer 60 is then inserted into housing 24 until it contacts seal 64. Thereafter, with housing 28 positioned so that seal 64 is aligned to enter mounting recess 66a in block 14, housing 28 is fastened in place by pushing actuator 32 into the end of housing 28 and tightening end cap 26 thereagainst. This fastening action occurs because, as previously explained, the slidable mounting of actuator 32 and spacer 60 permits them to transmit the force produced by the tightening of end cap 26 through to seals 64 and 66, between which housing 28 is positioned.

During the assembly process, actuator 32 should be oriented within housing 24, so that it may be coupled to pneumatic lines 40 and 42, via respective couplings 40a and 42a, through a further slot 43 in housing 24. If desired, the proper orientation of actuator 32 may be facilitated by providing a longitudinal guide groove in housing 24 and a mating projection on actuator 32.

One important advantage of slidably mounting elements 28, 32 and 60 in housing 24 is that this type of mounting allows the compressive force on both of seals 64 and 66 to be adjusted by simply tightening end cap 26 until the desired sealing pressure is reached. This adjustability of the seal pressure is beneficial since it allows the integrity of the seals to be restored as the original seal between metering rod 30 and seals 64 and 66 loosens as a result of wear. This, in turn, allows the seals to be replaced less frequently, thereby saving both the cost of the seals and of the downtime involved in replacing them. Significantly, all such adjustments in sealing pressure are accomplished without disassembling any part of loading assembly 10.

In most cases the thermal isolation provided by the above-described mounting and sealing arrangement for housing 28 will make unnecessary the provision of additional insulation between the outer surface of housing 28 and the adjacent inner surfaces of slots 24a and 24b. If, however, in a particular application it is found that the contact between housings 28 and 24 provides a path for excessive heat flow to housing 28, an insulating liner (not shown) may be provided between the inner surfaces of slots 24a and 24b and the adjacent outer surfaces of housing 28.

Sample evaporating assembly 12 will not be described. As is best seen in FIG. 2, sample evaporating assembly 12 includes a generally cylindrical housing 80 having a central chamber 82, into which carrier gas may be directed through a carrier gas flow passage 84 and from which sample-laden carrier gas may be removed through a passage 86. In the preferred embodiment, there is located within central chamber 82 a carrier gas flow control element 88 which will be described more fully presently. Optionally, evaporating assembly housing 80 may be provided with a conventional heating element 90 for maintaining housing 80 at a temperature high enough to assure the rapid vaporization of samples received from loading assembly 10.

Referring to FIG. 1, it will be seen that flow control element 88 has an elongated central section 88a having one diameter and first and second end sections 88b and 88c having another, greater diameter. Passing through the center of element 88 is an axial hole 88d having a diameter large enough to admit rod 30 and to provide a path for the flow of gas between rod 30 and element 88, when rod 30 is in its extended position. In addition, as is best seen in FIG. 2, the outer end of element 88 is provided with one or more generally radial holes 88e which provide a path for the flow of carrier gas between the outer surface of element 88 and axial hole 88d. This shape for element 88 causes carrier gas to flow through assembly 12 through the path including inlet passage 84, the outer surface of section 88a of element 88, holes 88e, axial hole 88d and outlet passage 86.

One important advantage of flow control element 88 is that it effectively extends inlet passage 84 toward loading assembly 10. This allows a flow of carrier gas to be directed against metering rod 30 from a position near the point at which rod 30 leaves seal 66, thereby minimizing the trapping of traces of sample in the "dead volume" between seal 66 and the carrier gas entry point at holes 88e. This also allows the portion of the carrier gas flow passage that comprises small diameter holes drilled through the main body of housing 80 to be relatively short and to be limited to the inner end of housing 80. In the present embodiment, such holes include two intersecting holes 84 and 84a, one of which is plugged to form a right angle bend in the gas flow passage joining inlet line 92 and internal chamber 82. As is best seen in FIG. 2, the latter holes are confined to the end of housing 80 that is on the high temperature side of wall 16. Thus, element 88 minimizes dead volume while eliminating the need for drilling holes through virtually the entire length of housing 80.

The advantage of eliminating a long gas flow passage through housing 80 is that it allows the use of a more advantageous shape for the outer end section of housing 80. As is best seen in FIG. 1, for example, the end of sample evaporating assembly 12 that projects into wall 16 preferably has a diameter that progressively decreases toward the end thereof. More particularly, the diameter of housing 80 decreases first to the diameter of step 80a and then to the diameter of step 80b. Those decreases in diameter are advantageous because they progressively decrease the rate at which housing 80 can conduct heat from high temperature region HT to low temperature region LT. This is because, as is well known, the rate of heat flow through an element that joins two regions of differing temperatures is directly proportional to the cross-sectional area of that element. In the case of housing 80, the cross-sectional area of end section 80b can be made as small as desired since no gas flow passages penetrate the side wall of that end section.

In addition to reducing the rate of heat flow between assemblies 10 and 12, the stepped configuration of the end of housing 80 allows one of the steps 80a to be provided with the previously mentioned threads 14b by which housing 80 is fastened to junction block 14. Still another advantage of using housing 80 with an end section of decreasing diameter is that, consistent with the above-described heat flow considerations, it permits housing 80 to extend far enough toward assembly 10 that it makes direct contact with and is directly sealed by seal 66.

Another important advantage of flow control element 88 is that it provides a structure in which there may be drilled a plurality of gas entry holes such as 88e that allow carrier gas to be directed against metering groove 30a from a number of different directions simultaneously. This is advantageous not only because it greatly increases the gas flow rate in the vicinity of groove 30a, but also because it assures that all points on the periphery of the metering groove are swept clean of the sample. Flow control element 88 also allows holes 88e to be drilled at any desired angle to metering rod 30. Holes 88e may, for example, be inclined so that their center lines do not intersect the center line of hole 88d. The latter configuration allows carrier gas to impact the sample in metering groove 30*a* with both radial and tangential components, i.e., with a swirling action, if desired.

Still another advantage of using flow control element 88 is that its removability assures that both it and the passages exposed by its removal may be conveniently cleaned. Naturally, after element 88 has been removed, it may be replaced by a flow control element having different holes sizes and configurations. This, in turn, allows the vaporization characteristics of the valve to be changed as necessary to accommodate test liquids having different flow characteristics.

As previously explained, during the sample injection process, the sample is blasted or ejected from groove 30*a* by the force of carrier gas stream flowing through holes 88*e* and becomes entrained in the carrier gas stream. The sample-bearing carrier gas stream then flows in the clearance space between metering rod 30 and the interior of axial hole 88*d* and exits assembly 12 through outlet passage 86 and line 94. In the preferred embodiment substantially none of the sample-bearing carrier gas will remain at the inner end of chamber 82 at the time that metering rod 30 completes its furthest inward travel into assembly 12. This is because, in the preferred embodiment, the end of metering rod 30 is arranged to stop only a short distance, such as 60 thousandths of an inch, from the junction of chamber 82 and passage 86. This short distance assures that there is virtually no "dead volume" at the inner end of axial hole 88*d* where traces of samples may linger to contaminate later injected samples. Also contributing to the minimization of the total dead volume at the inner end of housing 80 is the use of an outlet passage 86 having a total volume that is sufficiently small that it does not appreciably add to the above-mentioned dead volume within chamber 82. Thus, the geometries of rod 30, chamber 82 and passage 86 assure that the interior of sample evaporating assembly 12 has only a negligible dead volume.

In summary, it will be seen that a liquid sample injection valve constructed in accordance with the present invention is improved in a number of important respects over previously available sample injection valves. Firstly, it provides improved thermal isolation between the sample loading and sample evaporating assemblies thereof. Secondly, it greatly facilitates the removal and replacement of the metering rod and the adjustment of the pressure on the stripper seals. Thirdly, it includes a carrier gas flow control element which improves the gas flow characteristics of the valve and which facilitates the making of changes in those gas flow characteristics. Finally, it reduces the dead volume within the evaporating assembly to a level at which there is no substantial contamination of one sample by another.

What is claimed is:

1. In a liquid sample injection valve having a sample loading assembly and a sample evaporating assembly, the sample loading assembly including a metering rod for receiving a predetermined quantity of a sample liquid in the sample loading assembly and delivering that quantity of sample liquid to the sample evaporating assembly, an improved sample loading assembly including:
   (a) a main housing having first and second longitudinal slots therethrough,
   (b) a sample chamber housing projecting into the first and second longitudinal slots in the main housing, said sample chamber housing having a first passage for conducting a flow of the sample liquid and a second passage through which the metering rod may reciprocate between the sample loading and evaporating assemblies,
   (c) a linear actuator for producing reciprocating motion in the metering rod,
   (d) first and second stripper seals for stripping excess sample liquid from the metering rod, said seals being located at opposite ends of the sample chamber housing and serving to position the same within the main housing
   (e) said longitudinal slots providing a path through which air currents may flow over the sample chamber housing to cool the same.

2. A liquid sample injection valve as set forth in claim 1 in which the main housing includes a threaded end cap for closing the outer end thereof, and in which said linear actuator and sample chamber housing are slidably mounted within the main housing, whereby the tightening of said end cap produces a compressive force on said seals.

3. A liquid sample injection valve as set forth in claim 2 in which the metering rod penetrates the linear actuator and is fastened thereto only at the outer end thereof.

4. A liquid sample injection valve as set forth in claim 1 including a thermally nonconductive valve junction block located between the sample loading assembly and sample evaporating assembly, said block being fastened to the ends of said sample loading and evaporating assemblies to mount and separate the same.

5. A liquid sample injection valve as set forth in claim 4 in which said first and second seals are disposed between first and second recesses in said sample chamber housing and respective opposing recesses in the linear actuator and the valve junction block.

6. A liquid sample injection valve as set forth in claim 5 in which the thickness of the first seal is sufficient to provide a first air gap between the linear actuator and the sample chamber housing, said first air gap connecting said first and second longitudinal openings.

7. A liquid sample injection valve as set forth in claim 6 in which the thickness of the second seal is sufficient to provide a second air gap between the valve junction block and the sample chamber housing, said second air gap connecting said first and second longitudinal slots.

8. A liquid sample injection valve as set forth in claim 5 in which the thickness of the second seal is sufficient to provide a second air gap between the valve junction block and the sample chamber housing, said second air gap connecting said first and second longitudinal slots.

9. A liquid sample injection valve as set forth in claim 1 in which the metering rod penetrates the linear actuator and is fastened thereto only at the outer end thereof.

10. A liquid sample injection valve as set forth in claim in which the linear actuator is a pneumatic actuator which includes:
    (a) an actuator housing,
    (b) a piston assembly adapted to move between first and second positions in said actuator housing, said piston assembly having an axial hole penetrating the length thereof, and
    (c) means for fastening the metering rod to the outer end of the piston assembly, said fastening means being adapted to enable a user to detach the metering rod from the piston assembly.

11. A liquid sample injection valve as set forth in claim 10 in which the piston assembly includes a piston and a drive rod penetrating the piston and extending through both ends of the actuator housing, and in which said axial hole extends through said drive rod.

12. A liquid sample injection valve as set forth in claim 11 in which the fastening means comprises a mounting member adapted to threadedly engage the outer end of the drive rod.

13. A liquid sample injection valve as set forth in claim 10 in which the main housing includes a threaded end cap for closing the outer end thereof, and in which said linear actuator and sample chamber housing are slidably mounted within the main housing, whereby the tightening of said end cap produces a compressive force on said seals.

14. In a liquid sample injection valve having a sample loading assembly and a sample evaporating assembly, the sample loading assembly including a metering rod for receiving a predetermined quantity of a sample liquid in the sample loading assembly and delivering that quantity of sample liquid to the sample evaporating assembly, an improved metering rod drive assembly including:
    (a) a pneumatic actuator including
        (i) an actuator housing,
        (ii) a piston assembly adapted to move between first and second positions in said housing, said piston assembly having an axial hole penetrating the length thereof, and
    (b) means for fastening the metering rod to the outer end of the piston assembly, said fastening means being adapted to enable a user to detach the metering rod from the piston assembly without disassembling or disconnecting said pneumatic actuator.

15. A liquid sample injection valve as set forth in claim 14 in which the piston assembly includes a piston and a drive rod penetrating the piston and extending through both ends of the actuator housing, and in which said axial hole extends through said drive rod.

16. A liquid sample injection valve as set forth in claim 15 in which the fastening means comprises a mounting member adapted to threadedly engage the outer end of the drive rod.

* * * * *